（12）United States Patent
Rode et al.

(10) Patent No.: US 7,560,474 B2
(45) Date of Patent: Jul. 14, 2009

(54) DERIVATIVES OF PYRIDILETHANOL (PHENYLETHYL) AMINES AS INHIBITORS OF CHOLESTEROL BIOSYNTHESIS, PROCESS FOR THEIR PREPARATION AND PHARMACEUTICAL COMPOSITIONS CONTAINING THEM

(75) Inventors: Breda Rode, Kamnik (SI); Damjana Rozman, Ljubljana (SI); Klementina Fon Tacer, Ljubljana (SI); Darko Kocjan, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 16 days.

(21) Appl. No.: 10/521,294

(22) PCT Filed: Jul. 9, 2003

(86) PCT No.: PCT/SI03/00021

§ 371 (c)(1),
(2), (4) Date: May 24, 2005

(87) PCT Pub. No.: WO2004/007456

PCT Pub. Date: Jan. 22, 2004

(65) Prior Publication Data

US 2005/0256172 A1 Nov. 17, 2005

(30) Foreign Application Priority Data

Jul. 17, 2002 (SI) ................. 200200177
Nov. 28, 2002 (SI) ................. 200200287

(51) Int. Cl.
 *A61K 31/44* (2006.01)
 *C07D 213/24* (2006.01)
(52) U.S. Cl. ...................... 514/357; 546/334
(58) Field of Classification Search ................. 546/344, 546/334; 514/357
See application file for complete search history.

(56) References Cited

U.S. PATENT DOCUMENTS 2,786,846 A * 3/1957 Cislak et al. ................. 546/349
(Continued)

FOREIGN PATENT DOCUMENTS

EP 0 254 856 2/1988

OTHER PUBLICATIONS

Schultz et. al., "Synthesis of 1-(4-pyridyl)-2-amino-alkanoles", Archiv der Pharmazie, 1972, pp. 248-253.*
(Continued)

*Primary Examiner*—Janet L Andres
*Assistant Examiner*—Binta M Robinson
(74) *Attorney, Agent, or Firm*—Luedeka, Neely & Graham, P.C.

(57) ABSTRACT

The novel derivatives of pyridilethanol (phenylethyl) amines of formula I

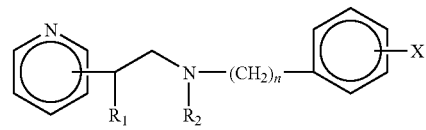

are described wherein n is an integer from 1 to 4, $R_1$ is a hydrogen atom, hydroxyl group or lower $C_{1-6}$alkoxy group $R_2$ is a hydrogen atom or a straight or branched lower $C_{1-6}$alkyl group X, is hydrogen, fluorine, chlorine, bromine, hydroxyl group, trifluoromethyl group, 3,4-di-Cl,2,4-di-Cl or lower $C_{1-6}$alkoxy group, the enantiomers, diastereoisomers or racemates thereof or the physiologically acceptable acid addition salts thereof which are ligands of sigma receptors for inhibiting cholesterol biosynthesis and are thus appropriate for the treatment of hypercholesterolemia and hyperlipemia in humans. The greatest lowering of cholesterol was observed by 1-(d-pyridyl)-2-(N-(2-(3,4-dicholorophenyl)ethyl-N-propylamino)ethanol in the form of dihydrobromide salt (signature BK-35, 2HBr).

10 Claims, 10 Drawing Sheets

U.S. PATENT DOCUMENTS 6,057,371 A    5/2000  Glennon

OTHER PUBLICATIONS

Schultz et. al., "Synthesis of 1-(4-pyridyl)-2-amino-alkanoles", Archiv der Pharmazie, 1972, pp. 248-258.*

1957:77176 Hcaplus Abstract, US Patent 2786846, Mar. 26, 1957, Cislak et. al.*

Moebius et al., "The Mysteries of Sigma Receptors: New Family Members Reveal a Role in Cholesterol Synthesis", Trends in Pharmacological Sciences, vol. 18, No. 3, pp. 67-70 (1997).

* cited by examiner

A

B

DERIVATIVES OF PYRIDILETHANOL (PHENYLETHYL) AMINES AS INHIBITORS OF CHOLESTEROL BIOSYNTHESIS, PROCESS FOR THEIR PREPARATION AND PHARMACEUTICAL COMPOSITIONS CONTAINING THEM

FIELD OF THE INVENTION

The present invention belongs to the area of the active substances from the group of heterocyclic compounds, and the pharmaceutical industry and it relates to the novel derivatives of pyridylethanol (phenylethyl) amine, the processes for their preparation, pharmaceutical compositions containing them, and to their use for inhibiting cholesterol biosynthesis. The novel derivatives of pyridylethanol (phenylethyl) amine according to the invention are the ligands of sigma receptors, inhibitors of cholesterol biosynthesis at the level of sterol Δ7,8-isomerase and are suitable for the treatment of hypercholesterolemia and hyperlipemia in humans.

TECHNICAL PROBLEM

There is a constant need for new active substances that inhibit cholesterol biosynthesis, effective antihypercholestrolemic and antihyperlipemic agents which would provide a more targeted action in the therapy and with fewer side effects in comparison to the active substances known in the prior art.

PRIOR ART

Because the high blood cholesterol level is a recognized risk factor in the onset of atherosclerosis, numerous investigations have been aimed at searching for a drug which would bring about reduced levels of blood cholesterol in the mammals and thus it would highly effective in the treatment of hypercholesterolemia and hyperlipemia. It has been established that lowering cholesterol biosynthesis by inhibitors of cholesterol biosynthesis is one of the modes of treatment.

Several inhibitors of cholesterol biosynthesis are known at the level of inhibition of 3-hydroxy-3-methylglutaryl-coenzyme A reductase (HMG-CoA reductase), as disclosed, for example, in U.S. Pat. No. 4,231,938 (lovastatin), U.S. Pat. No. 4,444,784 (simvastatin), U.S. Pat. No. 4,346,227 (pravastatin sodium) or U.S. Pat. No. 5,273,995 (atorvastatin) which are already used in the therapy and are the recognized commercial preparations Mevacor®, Sinvacor®, Lipitor®. These HMG-CoA reductase inhibitors, also known by the common name statins, significantly lower blood cholesterol levels.

Derivatives of pyridine-ethanolamine that are useful in the treatment of obesity and/or diabetes, especially in obese adult individuals, are known from U.S. Pat. No. 4,800,206.

It is known that sigma ligands bind to sigma receptors that are structure homologues of sterol Δ8,7-isomerase (F. F. Moebius et al, Brit. J. Pharmacol. (1997), 121, 1-6) and belong to the last portions of cholesterol biosynthesis. However, there are no active substances or drugs known in the current medicine that would inhibit cholesterol biosynthesis at the level of sterol Δ8,7-isomerase.

Problem Solution Description Including Examples

The aim of the present invention is to find new active substances that would significantly lower the level of blood cholesterol in the mammals by inhibiting cholesterol biosynthesis in the last portions of its biosynthesis pathway, that is, at the level of sterol Δ7,8-isomerase, thus, have a more selective inhibitory action than the action of known statins which inhibit HMG-CoA reductase in the early portion of cholesterol biosynthesis pathway.

The use of the novel compounds of this invention would permit a more targeted therapeutic action with fewer side effects in comparison with the active substances already approved in the therapy.

This problem has been solved by the present invention which relates to novel pyridylethanol (phenylethyl) amine derivatives, to the processes for their preparation, to the pharmaceutical compositions containing them and the use of the compounds in accordance with the invention for the treatment of hypercholesterolemia and hyperlipemia.

New pyridylethanol (phenylethyl) amines of this invention are compounds of general formula I

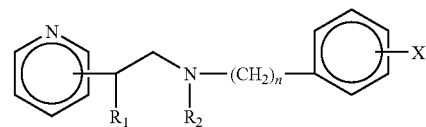

wherein n is an integer from 1 to 4

$R_1$ is a hydrogen atom, hydroxyl group or lower $C_{1-6}$ alkoxy group $R_2$ is a hydrogen atom or a straight or branched lower $C_{1-6}$ alkyl group X is hydrogen, fluorine, chlorine, bromine, hydroxyl group, trifluoromethyl group, 3,4-di-Cl, 2,4-di-Cl or lower $C_{1-6}$ alkoxy group as well the physiologically acceptable acid addition salts thereof.

The term lower alkyl group denotes straight- or branched-chain lower alkyl group with 1 to 6, preferably 1 to 4, carbon atoms ($C_{1-6}$ alkyl) such as methyl, ethyl, n-propyl, isopropyl, n-butyl and isobutyl group. The term lower alkoxy group denotes alkoxy group with 1 to 6, preferably 1 to 4, carbon atoms ($C_{1-6}$ alkoxy) such as methoxy, ethoxy, propoxy, isopropoxy, butoxy and isobutoxy group.

The compounds of formula I form salts with acids and these salts are also the part of the invention. Examples of such salts are the salts with physiologically compatible mineral acids such as, for example, hydrochloric acid, hydrobromic acid, phosphoric acid; or with organic acids such as, for example, methanesulfonic acid, citric acid, oxalic acid, maleic acid, benzenesulfonic acid and others.

New compounds of this invention contain at least one asymmetric carbon atom and can, therefore, exist as optically active enantiomers, as diastereomers or as racemates.

The compounds of formula I in which n=2 and in which $R_1$ is a hydroxyl group, $R_2$ is a methyl or n-propyl group and X is a hydrogen atom or two atoms of chlorine in the positions 3 and 4 of the phenyl nucleus, are the novel derivatives of pyridylethanol (phenylethyl) amine and are the preferred compounds in accordance with the invention.

Of the compounds, mentioned above, preferred compound are:

1-(3-pyridyl)-2-(N-(2-phenylethyl)-N-propylamino)ethanol and a dihydrobromide salt of formula II thereof (signature BK-31 in descriptions and figures)

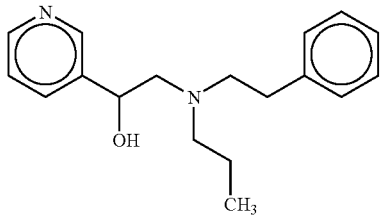

1-(3-pyridyl)-2-(N-(2-(3,4-dichlorophenyl)ethyl)-N-methylamino)ethanol and a dihydrobromide salt of formula III thereof (signature BK-33 in descriptions and figures)

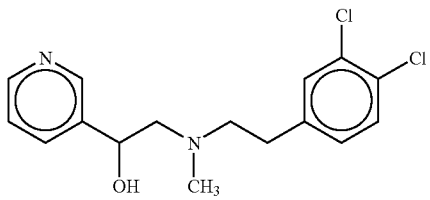

1-(3-pyridyl)-2-(N-(2-(3,4-dichlorophenyl)ethyl)-N-propylamino)ethanol and a dihydrobromide salt of formula IV thereof (signature BK-35 in descriptions and figures)

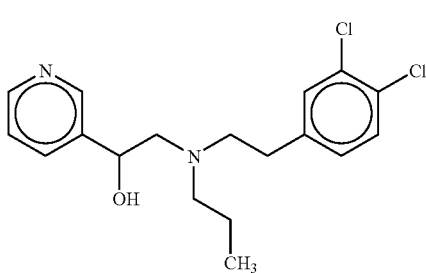

and 1-(4-pyridyl2-(N-(2-(3,4-dichlorophenyl)ethyl)-N-methylamino)ethanol and a dihydrobromide salt of formula V thereof (signature BK-38 in descriptions and figures)

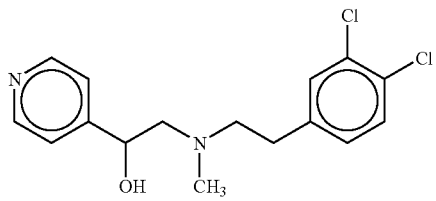

Of the above mentioned compounds of this invention especially preferred compound is 1-(3-pyridyl)-2-(N-(2-(3,4-dichlorophenyl)ethyl)-N-propylamino)ethanol and a dihydrobromide salt (BK-35.2HBr) thereof as an inhibitor of cholesterol biosynthesis and thus appropriate for the treatment of hypercholesterolemia and hyperlipemia.

The compounds of this invention may be prepared in two different ways which are shown in the following scheme as variant (a) and variant (b):

Variant a):
alkylating secondary amines of formula VI $$NHR_2CH_2CH_2Z \qquad \qquad VI$$

wherein $R_2$ is as defined above and Z is a group

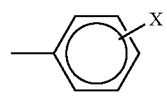

wherein X is as defined above, with pyridyloxirane (pyridyl ethylene oxide) of formula VII

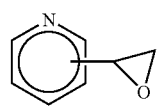

to the desired title pyridylethanol (phenylethyl) amines of formula I and, if desired, converting them into to the physiologically acceptable acid addition salts thereof.

Secondary amines of formula VI may be prepared by alkylating primary amines of formula XII $$H_2N-CH_2CH_2Z \qquad \qquad XII$$

with alkyl iodides of formula XIII $$R_2J \qquad \qquad XIII$$

according to the following reaction scheme:

wherein substituents $R_2$ and Z are as defined above.

Primary amines of formula XII and alkyl iodides of formula XIII are known and commercially available chemicals.

At 2-, 3- or 4-substituted pyridyloxirane of formula VII in the process of alkylating secondary amines of formula VI is prepared in situ by transformation at 2-, 3- or 4-substituted bromo-acetylpyrine hydrobromide with complexed metal hydrides, such as sodium boronhydride in an inert solvent such as lower aliphatic alkanol, for example, ethanol at a temperature about room temperature.

At 2-, 3- or 4-substituted bromo-acetylpyridine hydrobromide is prepared by transformation of the original at 2-, 3- or 4-substituted acetylpyridine which are known and commercially available chemicals for bromination with bromine and hydrobromic acid.

The alkylation step of secondary amines of formula VI with pyridyloxirane of formula VII is carried out at a temperature of about room temperature to reflux temperature of the reaction mixture, in an inert solvent such as lower aliphatic alkanol, for example, ethanol. The crude pyridylethanol (phenylethyl) amines of formula I formed are isolated and purified by common procedures known in the prior art, preferably by column chromatography.

Variant (b):

Alkylating primary amines of formula VIII

wherein $R_2$ is as defined above, with pyridyloxirane of formula VII

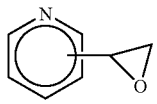

VII to intermediate compounds of formula IX

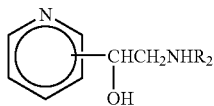

IX wherein $R_2$ is as defined above, and condensing with the derivatives of phenyl acetic acid of formula X

X wherein Z is as defined above, to new intermediate compounds of formula XI

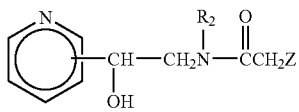

XI wherein substituents $R_2$ and Z are as defined above, and reducing them to the desired title pyridylethanol (phenylethyl) amines of formula I, and, if desired, converting them into the physiologically acceptable acid addition salts thereof.

Primary aliphatic amines of formula VIII, such as methylamine or n-propylamine, are known and commercially available chemicals which are alkylated with pyridyloxirane of formula VII in an inert solvent, such as lower aliphatic alkanol, for example ethanol, to intermediate compounds of formula IX. These intermediate compounds are condensed with the derivatives of phenyl acetic acid of formula X wherein a substituent Z is as defined above, in an inert solvent and at a temperature about room temperature. Condensing agents known in the art may be used as a condensing agent, such as dicyclohexylcarbodiimide (DCC), as an inert solvent, for example, methylene chloride (dichloromethane).

In the final step of the synthesis, a carbonyl group in the novel intermediary compounds XI is reduced to an alcohol group. The reaction is carried out with conventional reducing agents, preferably with those suitable for reduction of the carbonyl group to the group —$R_2$HN—CO—. Especially suitable is a complex metal hydride, such as $LiAlH_4$ in an inert solvent, preferably in ether, such as tetrahydrofuran (THF), diethyl ether, dioxane and similar. The desired title pyridylethanol (phenylethyl) amines of formula I formed are isolated and purified in a conventional manner, preferably by column chromatography on silica gel and then, if desired, they are converted into the physiologically acceptable acid addition salts thereof.

The processes for preparation of the novel derivatives of pyridylethanol (phenylethyl) amine of formula I in accordance with the variants (a) and (b) are shown in FIG. 5.

The synthesis of the novel derivatives of pyridylethanol (phenylethyl) amines of formula I in which $R_1$ is a hydrogen atom may be performed so that the novel compounds of formula I in accordance with the invention wherein $R_1$ is a hydroxyl group, are first acetylated in a conventional manner, for example, with acetanehydride and then the O-acetyl compound formed is catalytically hydrogenated by common methods, such as, with palladium on a carrier, for example, barium sulfate, according to the following variant c)

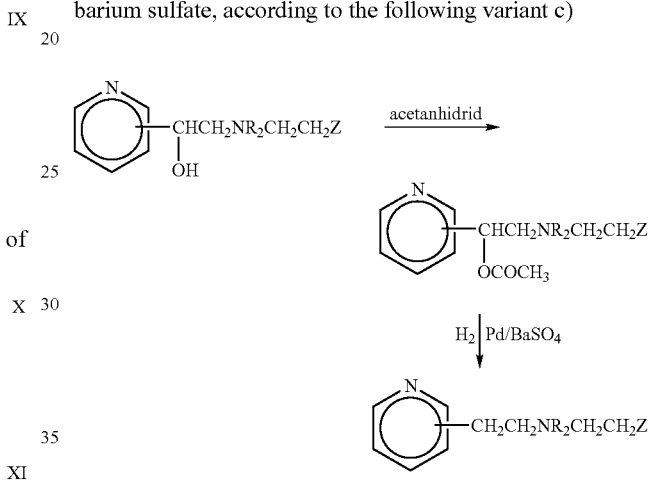

By the other variant the novel derivatives of pyridylethanol (phenylethyl) amine of formula I may be prepared wherein R1 represents a hydrogen atom, according to the following variant d)

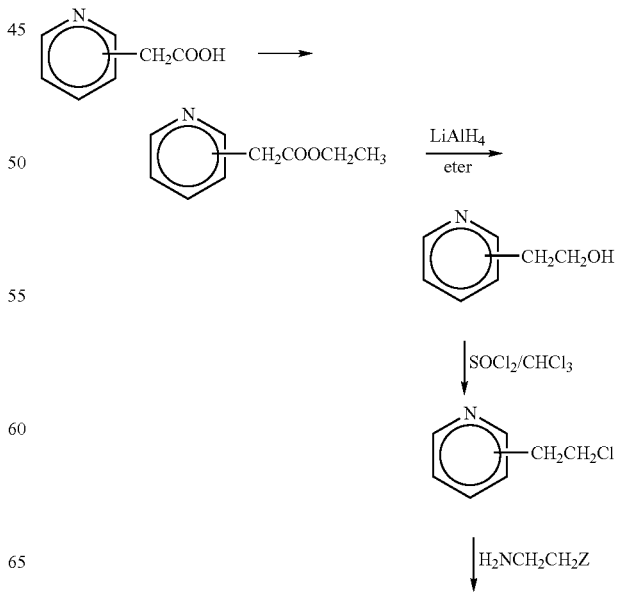

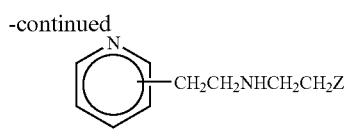

The original at 2-, 3- or 4-substituted pyridyl acetic acid is esterified in a conventional manner known in the prior art, for example, by transforming it to ethyl ester of pyridylacetic acid thereof which is then reduced with conventional reductants, preferably with those for reduction of the ester group to an alcohol group. Particularly suitable is a complexed metal hydride, such as lithium aluminum hydride (LiAlH$_4$) in an inert solvent, preferably in ether, such as diethyl ether, tetrahydrofuran, dioxane and the like. By this procedure produced 2, 3 or 4-substituted pyridyl ethanol is transformed to 2-, 3- or 4-substituted pyridyl ethylenechloride with common chlorinating agents, such as thionyl chloride in an inert solvent, such as chloroform. The produced substituted pyridylethylene chloride is used to alkylate primary amines of formula VI to produce the title derivatives of pyridylethanol (phenylethyl) amines of formula I wherein R$_1$ represents a hydrogen atom.

In accordance with the invention goal, the effect of the novel derivatives of pyridylethanol (phenylethyl) amine as ligands of sigma receptors on inhibition of cholesterol biosynthesis was assessed. An ex vivo method of metabolic labeling of immortal human hepatocytes was employed. The radioactively labelled early precursor of cholesterol [$^3$H] acetate was added to cells with or without addition of sigma ligands. Two independent experiments of metabolic labeling and sterol analysis were performed. The results of both analyses are reproducible and show that the tested substances significantly lower cholesterol synthesis.

Of novel ligands of sigma receptors of this invention, the highest potential to inhibit cholesterol biosynthesis is exhibited by the substance 1-(3-pyridyl-2-(N-(2-(3,4-dichlorophenyl)ethyl)-N-propylamino)ethanol, in the form of dihydrobromide salt (signature BK 35.2HBr).

Recently, it has been established that sigma ligands bind to sigma receptors that are structure homologues of sterol Δ8,7-isomerase since they belong to the same gene family. Sterol Δ8,7-isomerase contributes to the late portion of cholesterol biosynthesis, as evident from FIG. 1. FIG. 1 shows that the most commonly used substrates are Δ8-cholestenol and zymosterol which differ in the saturation of the side chain at position Δ24,25. FIG. 2 represents cholesterol biosynthesis with marked sites of action of inhibitors of cholesterol biosynthesis.

The effect of novel pyridylethanol (phenylethyl) amines as sigma ligands in accordance with the invention is more selective than the effect of statins, used in the therapy, such as lovastatin or pravastatin, which inhibit HMG-CoA reductase that belongs to the early portion of cholesterol biosynthesis.

With novel pyridylethanol (phenylethyl) amines of this invention a more selective action with fewer side effects is provided due to the inhibition of cholesterol biosynthesis in late steps of this biosynthesis pathway. Consequently, these substances are particularly useful for the treatment of hypercholesterolemia and hyperlipemia. These effects of the novel pyridinylethanol (phenylethyl) amines were truly unexpected as insofar in medical practice and therapy lack of substances that would lower cholesterol level by targeting enzymes in late steps of cholesterol biosynthesis.

Application of the novel pyridylethanol (phenylethyl) amines of formula I of this invention markedly decreases the pathologically increased blood cholesterol levels in treated patients. The dosage and frequency of application depend on the characteristics of an individual drug, its bioavailability and pharmacokinetic characteristics, and the patient's condition.

Pharmaceutical preparations contain the active substance together with the physiologically compatible organic or inorganic support, such as water, lactose, starch and its derivatives, magnesium stearate, talc, plant oils and similar. Pharmaceutical preparations are preferably administered orally, such as in the form of tablets, capsules, pills, powders, granulates, solutions, syrups, suspensions, elixirs and similar. Administration can be also carried out parenterally, for example, in the form of sterile solutions, suspensions or emulsions. Pharmaceutical preparations can be sterilized and/or include ingredients, such as, preservatives, stabilizers, emulsifiers, buffering substances and other additives.

The present invention is illustrated but in no way limited by the following examples:

EXAMPLE 1

1-(3-pyridyl)-2-(N-(2-phenylethyl)-N-propylamino) ethanol (BK 31)

Preparation of the starting compounds:
N-propyl-(β-phenylethyl)amine
1.2 ml (9.5 mmol) of phenylethylamine, 0.93 ml (9.5 mmol) of n-propyl-iodide, 5 ml of triethylamine and 5 ml of THF (tetrahydrofuran) were placed in a flask, and the reaction mixture was heated at reflux temperature of the reaction mixture for 3.5 hours and then cooled. A salt formed was filtered off, the solution was evaporated and a desired compound was purified by column chromatography on silica gel (silica gel 60, mobile phase: CHCl$_3$:CH$_3$OH=10:3). This yields 0.62 g (40%) of N-propyl-(β-phenylethyl)amine in the form of the oil (molecular weight: 163.264, formula: C$_{11}$H$_{17}$N).

3-bromoacetylpyridine hydrobromide
To 10 g (82.5 mmol) of 3-acetylpyridine was added 30 ml of 48% hydrobromic acid. The reaction mixture was heated to 70° C., and 4.2 ml of bromine was added dropwise with stirring. After completed addition of bromine, the reaction mixture was stirred further for 15 minutes at the same temperature and cooled on ice. A crystalline compound formed was filtered off and thoroughly washed with acetone. This yields 21 g (90%) of 3-bromoacetylpyridine hydrobromide, melting point 195-200° C.

Preparation of the Title 1-(3-pyridyl)-2-(N-(2-phenylethyl)-N-propylamino)ethanol
To 1.01 g (3.6 mmol) of 3-bromoacetylpyridine hydrobromide was added 20 ml of absolute ethanol and 0.5 g (13.2 mmol) of sodium boronhydride. The reaction mixture was stirred at 20° C. for 2 hours, filtered and to the filtrate containing 3-pyridyloxirane was added 0.96 g (5.9 mmol) of N-propyl-(β-phenylethyl)amine. The reaction mixture was heated at reflux temperature of the reaction mixture for 4 hours and evaporated to a dry residue, and to it was added 20 ml of chloroform. A solid portion was filtered off, the filtrate was evaporated, and an oil residue formed was purified by column chromatography on silica gel (silica gel 60, mobile phase: CHCl$_3$:CH$_3$OH=10:3). This yields 0.56 g (55%) of the title compound in the form of the oil base.

0.56 g (2 mmol) of a purified oil base of 1-(3-pyridyl)-2-(N-(2-phenylethyl)-N-propylamino)ethanol was dissolved in 5 ml of acetone. The resulting solution was cooled on ice, and with stirring 2.5 ml of etahnolic solution of hydrobromic acid solution (0.35 g (4.3 mmol HBr)) was added. To a precipitate formed was added 3 ml of diethyl ether. After stirring for 2 hours on ice, a crystalline product was filtered off and washed with diethyl ether. This yields 0.7 g (80%) of 1-(3-pyridyl)-2-(N-(2-phenylethyl)-N-propylamino)ethanol dihydrobromide, melting point 113-120° C. (molecular weight: 446.238, gross formula: $C_{18}H_{24}N_2O.2HBr$).

$^1$H NMR spectrum, $D_2O$, ppm according to DSS (0 ppm): 8.89, 8.80 (2H), 8.65, 8.57 (1H), 8.10 (1H), 7.38 (5H), 5.47 (1H), 3.7-3.1 (8H), 1.80 (2H), 0.97 (3H).

IR (infra-red) spectrum (KBr disc) is shown in FIG. 6.

EXAMPLE 2

1-(3-pyridyl)-2-(N-(2-(3,4-dichlorophenyl)ethyl)-N-metylamino)ethanol (BK 33)

Preparation of 1-(3-pyridyl)-2-metylaminoethanol

To 1.01 g (3.6 mmol) of 3-bromoacetylpyridine hydrobromide, prepared as described in Example 1, was added 20 ml of absolute ethanol and 0.5 g (13.2 mmol) of sodium boronhydride, a reaction mixture was stirred at 20° C. for 2 hours and filtered. To a filtrate containing 3-pyridyloxirane was added 1.3 ml of 33% ethanolic solution of methylamine and heated at reflux temperature of the reaction mixture for 5 hours. The reaction mixture was then evaporated to a dry residue and to it was added 20 ml of chloroform. A solid portion was filtered off, the filtrate was evaporated and an oil residue formed was purified by column chromatography on silica gel (mobile phase: $CHCl_3:CH_3OH=10:3$). This yields 0.33 g (60%) of a title compound in the form of the oil base (molecular weight: 152.196, gross formula: $C_8H_{12}N_2O$).

Preparation of 1-(3-pyridyl)-2-(N-(2-(3,4-diclophenyl)acetyl-N-metylamino)ethanol To a flask containing 542 mg (2.6 mmol) of DCC (dicyclohexylcarbodiimide) was added 2 ml of methylene chloride, and a solution of 538 mg (2.6 mmol) of 3,4-dichlorophenyl acetic acid in 3 ml of methylene chloride was added dropwise with stirring resulting in the formation of a precipitate. After stirring for 5 minutes, 400 mg (2.6 mmol) of 1-(3-pyridyl)-2-methylaminoethanol was added to the reaction mixture and stirred further for 1 hour at 20° C. A precipitate formed was filtered off and the solution was evaporated. The evaporated filtrate was purified by column chromatography on silica gel (silica gel 60, mobile phase: $CHCl_3:CH_3OH=10:0.5$). This yields 715 mg (80%) of 1-(3-pyridyl)-2-(N-(2-(3,4-dichlorophenyl)acetyl-N-methylamino)ethanol (molecular weight: 339.224, gross formula: $C_{16}H_{16}N_2O_2Cl_2$)

Preparation of the Title 1-(3-pyridyl)-2-(N-(2-(3,4-dichlorophenyl)ethyl-N-methylamino)ethanol (BK-33)

0.53 g (13.9 mmol) of lithium aluminum hydride ($LiAlH_4$) was placed into a flask, 6 ml of anhydrous tetrahydrofuran (THF) was added and a mixture was cooled on ice. To the reaction mixture was added dropwise with stirring a solution of 1.1 g (3.2 mmol) of 1-(3-pyridyl)-2-(N-(2-(3,4-dichlorophenyl)acetyl)-N-ethylamino) ethanol in 10 ml of anhydrous tetrahydrofuran (THF). After completed addition, the reaction mixture was stirred further for 1 hour at 20° C., cooled on ice and with vigorous stirring was added stepwise 6.5 ml of 15% NaOH and then 16 ml of methylene chloride ($CH_2Cl_2$). An organic phase was separated, dried on anhydrous $Na_2SO_4$ and evaporated on a rotavapor resulting in the formation of an oil residue which was then purified by column chromatography on silica gel (silica gel 60, mobile phase: $CH_3OH:ethyl\ acetate=10:2$). This yields 0.63 g (60%) of a title compound in the form of the oil base.

0.60 g (1.84 mmol) of a purified oil base was dissolved in 3.5 ml of acetone. The solution was cooled on ice and with stirring was added 2.4 ml of ethanolic solution of hydrobromic acid (0.328 g HBr; 4.1 mmol). To a residue formed was added 2 ml of diethyl ether. After stirring the reaction mixture for 2 hours on ice, a crystalline product formed was filtered off and washed with diethyl ether. This yields 0.72 g (80%) of 1-(3-pyridyl)-2-(N-(2-(3,4-dichlorophenyl)ethyl)-N-methylamino)ethanol dihydrobromide, melting point 157-161° C. (molecular weight: 487.074, gross formula: $C_{17}H_{18}N_2OCl_2.2HBr$).

$^1$H NMR spectrum; $D_2O$, ppm according to DSS (0 ppm): 8.90 (1H), 8.78 (1H), 8.64 (1H), 8.10 (1H), 7.50 (2H), 7.24 (1H), 5.50 (1H), 3.52 (4H), 3.08 (5H).

IR spectrum (KBr disc) is shown in FIG. 9.

EXAMPLE 3

1-(3-pyridyl)-2-(N-(2-(3,4-diclorophenyl)ethyl)N-propylamino)ethanol (BK-35)

Preparation of 1-(3-pyridyl)-2-propylaminoethanol

To 1.01 g (3.6 mmol) of 3-bromoacetylpyridine hydrobromide, prepared as described in Example 1, was added 20 ml of absolute ethanol and 0.5 g (13.2 mmol) of sodium boronhydride ($NaBH_4$). The reaction mixture was stirred at 20° C. for 2 hours and filtered. To the filtrate containing 3-pyridyloxirane was added 0.7 ml (8.5 mmol) of n-propylamine and heated at reflux temperature of the reaction mixture for 5 hours. The reaction mixture was then evaporated to a dry residue and to it was added 20 ml of chloroform, a solid portion was filtered off, the filtrate was evaporated and an oil residue formed was purified by column chromatography on silica gel (silica gel 60, mobile phase: $CHCl_3:ethyl\ acetate=10:2$). This yields 0.33 g (50%) of 1-(3-pyridyl)-2-propylaminoethanol in the form of the oil base (molecular weight: 180.25, gross formula: $C_{10}H_{16}N_2O$)

Preparation of 1-(3-pyridyl)-2-(N-(2-(3,4-dichlorophenyl)acetyl)-N-propylamino)ethanol To a flask containing 630 mg (3.1 mmol) of DCC (dicyclohexylcarbodiimide) was added 3 ml of methylene chloride and with stirring a solution of 625 mg (3.1 mmol) of 3,4-dichlorophenyl acetic acid in 5 ml of methylene chloride was added dropwise resulting in the formation of a precipitate. The reaction mixture was stirred for 5 minutes, and to it was added 550 mg (3.05 mmol) of 1-(3-pyridyl)-2-methylaminoethanol in 6 ml of methylene chloride, it was stirred further for 1 hour at 20° C. A precipitate formed was filtered off, and the resulting solution was evaporated. The evaporated filtrate was purified by column chromatography on silica gel (silica gel 60, mobile phase: $CHCl_3:CH_3OH=10:0.5$). This yields 0.56 g (50%) of 1-(3-pyridyl)-2-(N-(2-(3,4-dichlorophenyl)acetyl)-N-propylamino)ethanol in the form the oil (molecular weight: 367.278, gross formula: $C_{18}H_{20}N_2O_2Cl_2$).

Preparation of the Title 1-(3-pyridyl)-2-[N-(2-(3,4-dichlorophenyl)ethyl)-N-propylamino]ethanol (BK-35)

0.43 g (11.3 mmol) of lithium aluminum hydride ($LiAlH_4$) was placed into a flask, 6 ml of anhydrous tetrahydrofuran (THF) was added and a mixture was cooled on ice. To the reaction mixture was added dropwise with stirring a solution of 1 g (2.7 mmol) of 1-(3-pyridyl)-2-(N-(2-(3,4-dichlorophenyl)acetyl)-N-propylamino)ethanol in 10 ml of anhydrous THF. After completed addition, the reaction mixture was further stirred for 1 hour at 20° C., cooled on ice and with vigorous stirring 6.4 ml of 15% NaOH was added stepwise and then 16 ml of methylene chloride. An organic phase was separated, dried on anhydrous $Na_2SO_4$ and evaporated on a rotavapor. The evaporated residue was purified by column chromatography on silica gel (silica gel 60, first mobile phase: $CHCl_3:CH_3OH=10:0.5$; second mobile phase: ethyl acetate: $CH_3OH=10:1.5$). This yields 0.58 g (60%) of a title compound in the form of oil base.

0.50 g (1.4 mmol) of an obtained purified oil base was dissolved in 4 ml of acetone. The resulting solution was cooled on ice and with stirring was added 1.1 ml of ethanolic solution of hydrobromic acid (0.25 g HBr; 3.1 mmol). A white precipitate was formed and to it was added 3 ml of diethyl ether and after stirring on ice for 2 hours, a crystalline product formed was filtered off and washed with diethyl ether. This yields 0.62 g (85%) of 1-(3-pyridyl)-2-(N-(2-(3,4-dichlorophenyl)ethyl)-N-propylamino)ethanol dihydrobromide, melting point 198-202° C. (molecular weight: 515.124; gross formula: $C_{18}H_{22}N_2OCl_2.2HBr$)

$^1H$ NMR spectrum, $D_2O$, ppm according to DSS (0 ppm): 8.91 (1H), 8.81 (1H), 8.64 (1H), 8.12 (1H), 7.54 (2H), 7.27 (1H), 5.50 (1H), 3.58 (2H), 3.48 (2H), 3.34 (2H), 3.16 (2H), 1.82 (2H), 1.00 (3H)

IR spectrum (KBr disc) is shown in FIG. 8.

EXAMPLE 4

1-(4-pyridyl)-2(N-(2-(3,4-dichlorophenyl)ethyl)-N-methylamino)ethanol (BK-38)

Preparation of 1-(4-pyridyl)-2-methylaminoethanol

To 1.01 g (3.6 mmol) of 4-bromoacetylpyridine hydrobromide, prepared as described in Example 1, was added 20 ml of absolute ethanol and 0.5 g (13.2 mmol) of sodium boronhydride, and the reaction mixture was stirred at 20° C. for 2 hours, then filtered and to the filtrate containing 4-pyridyloxirane was added 1.3 ml 33% ethanolic solution of methylamine. The reaction mixture was heated at reflux temperature of the reaction mixture for 3 hours, evaporated to a dry residue and to it was added 20 ml of chloroform, and a solid portion was filtered off. The filtrate was evaporated and an obtained oil residue was purified by column chromatography on silica gel (silica gel 60, mobile phase: $CHCl_3$:ethyl acetate=10:2). This yields 0.30 g (55%) of a title compound in the form of the oil base (molecular weight: 152.196, gross formula: $C_8H_{12}N_2O$).

Preparation of 1-(4-pyridyl)-2-(N-(2-(3,4-dichlorophenyl) acetyl)-N-methylamino)ethanol To a flask containing 0.54 g (2.6 mmol) of DCC (dicyclohexylcarbodiimide) was added 2 ml of methylene chloride and 0.54 g (2.6 mmol) of 3,4-dichlorophenyl acetic acid in 4 ml of methylene chloride was added dropwise to produce the precipitate. The reaction mixture was stirred for 5 minutes and 400 mg (2.6 mmol) of 1-(4-pyridyl)-2-methylaminoethanol in 3 ml of methylene chloride was added and was stirred further for 1 hour at 20° C. A precipitate formed was filtered off, and the resulting solution was evaporated. The evaporated filtrate was purified by column chromatography on silica gel (silica gel 60, mobile phase: $CHCl_3:CH_3OH=10:0.5$). This yields 0.53 g (60%) of 1-(4-pyridyl)-2-(N-(2-(3,4-dichlorophenyl)acetyl)-N-methylamino)ethanol.

Preparation of the Title 1-(4-pyridyl)-2-[N-(2-(3,4-dichlorophenyl)ethy)-N-methylamino]ethanol (BK-38)

510 mg (13.5 mmol) of lithium aluminum hydride (LiAlH$_4$) was placed into a flask, 6 ml of anhydrous THF was added and a mixture was cooled on ice. To the reaction mixture was added dropwise with stirring a solution of 1.02 g (3 mmol) of 1-(4-pyridyl)-2-(N-(2-(3,4-dichlorophenyl) acetyl)-N-methylamino)ethanol in 10 ml of anhydrous THF. After completed addition, the reaction mixture was further stirred for 1 hour at room temperature, cooled on ice and with vigorous stirring 6.6 ml of 15% NaOH was added stepwise and then 16 ml of methylene chloride. An organic phase was separated, dried on anhydrous $Na_2SO_4$ and evaporated on a rotavapor to an oil residue which was purified by column chromatography on silica gel (silica gel 60, mobile phase: $CHCl_3:CH_3OH=10:1$. This yields 0.54 g (55%) of a title compound in the form of oil base.

0.50 g (1.54 mmol) of a purified oil base was dissolved in 3 ml of acetone. The resulting solution was cooled on ice and with stirring was added 1.8 ml of ethanolic solution of hydrobromic acid (0.274 g HBr; 3.4 mmol). A precipitate was formed and to it was added 3 ml of diethyl ether. After stirring the reaction mixture on ice for 2 hours, a crystalline product formed was filtered off and washed with diethyl ether. This yields 0.64 g (85%) of 1-(4-pyridyl)-2-(N-(2-(3,4-dichlorophenyl)ethyl)-N-methylamino)ethanol dihydrobromide, melting point 191-194° C. (molecular weight: 487.074; gross formula: $C_{17}H_{18}N_2OCl_2.2HBr$)

$^1H$ NMR spectrum, $D_2O$, ppm according to DSS (0 ppm): 8.81 (2H), 8.14 (2H), 7.47 (2H), 7.22 (1H), 5.54 (1H), 3.50 (4H), 3.08 (5H)

IR spectrum (KBr disc) is shown in FIG. 7.

EXAMPLE 5

Testing of four sigma ligands, (BK-31.2HBr, BK-33.2HBr, BK-35.2HBr and BK-38.2HBr) from examples 1 to 4, inhibitors of cholesterol biosynthesis as the level of sterol Δ7,8-isomerase The inhibitory effect on cholesterol biosynthesis of our novel ligands of sigma receptors BK-31.2 HBr, BK-33.2HBr, BK-35.2HBr and BK-38.2HBr), prepared according to examples 1 to 4, was evaluated. An ex vivo method of metabolic labeling of immortal human hepatocytes was applied. The radiolabel led precursor of cholesterol biosynthesis [$^3H$] acetate was added to the cells with or without the addition of sigma ligands. Finally, two independent experiments of metabolic labeling and sterol analysis were performed for each compound.

BRIEF DESCRIPTION OF THE DRAWINGS

Various features, aspects, and advantages of the present disclosure will be further shown or described by reference to the following detailed description, appended claims, and accompanying drawing figures and/or illustrations, wherein features are not to scale so as to more clearly show details, wherein like reference numbers refer to like or similar features throughout the several views, and wherein:

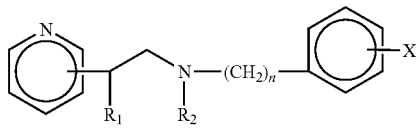

Figure 1:
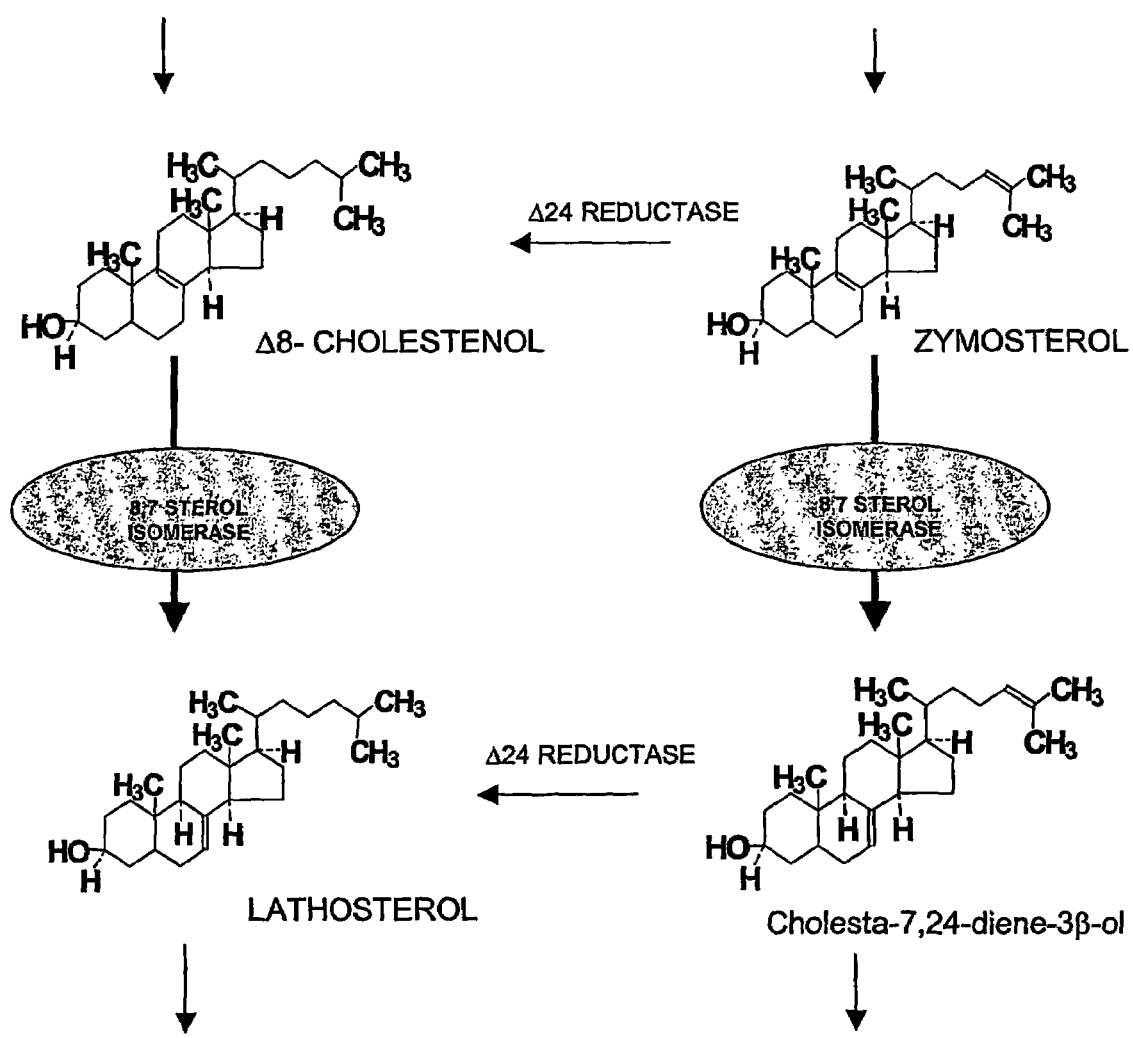
FIG. 1 is a schematic diagram showing aspects of cholesterol biosynthesis in which commonly used substrates Δ8-cholesterol and zymosferol differ in saturation of the side chain at position Δ24, 25.
Figure 2:
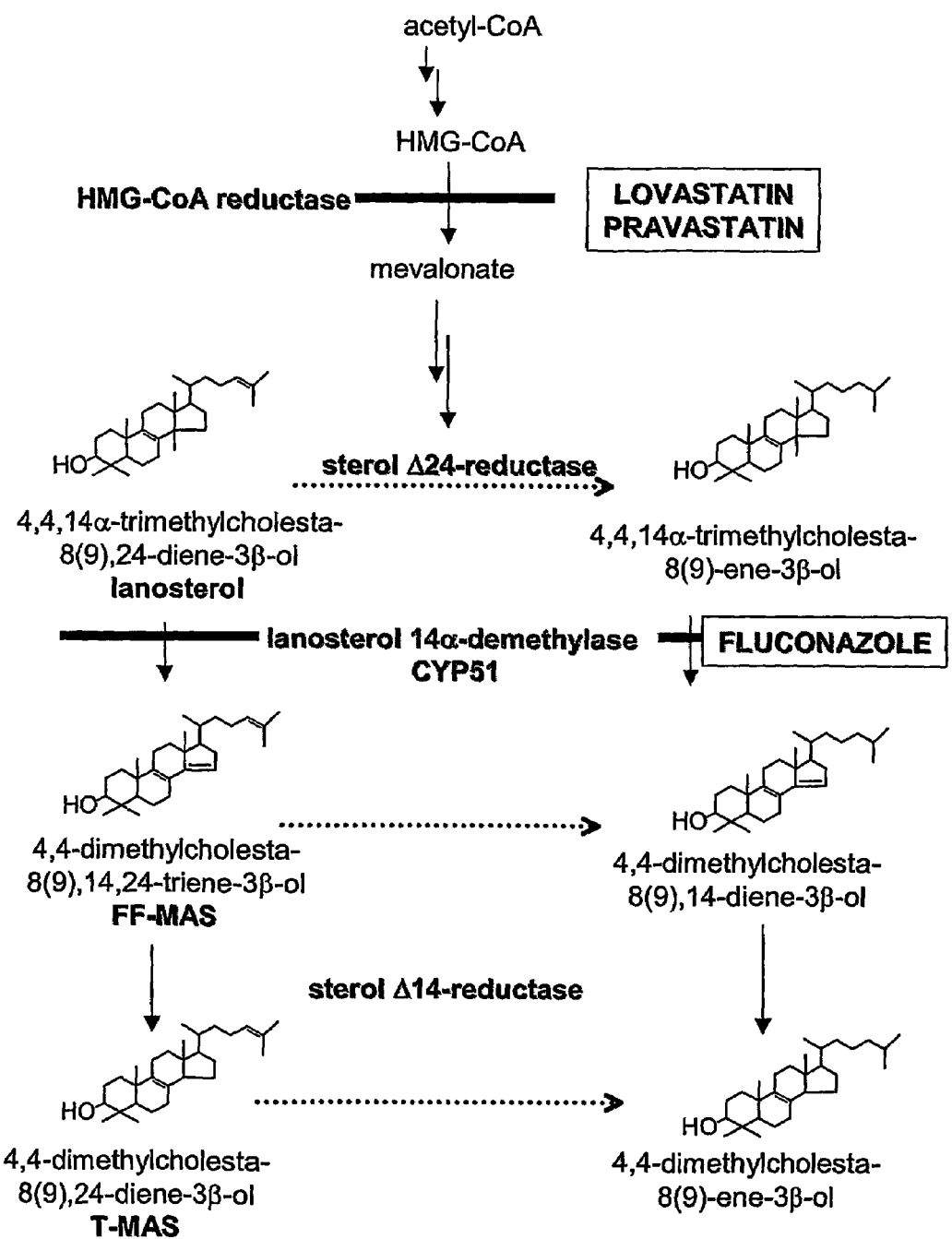
FIG. 2 is a schematic diagram showing aspects of cholesterol biosynthesis in which sites of action of inhibitors are marked.
Figure 2:
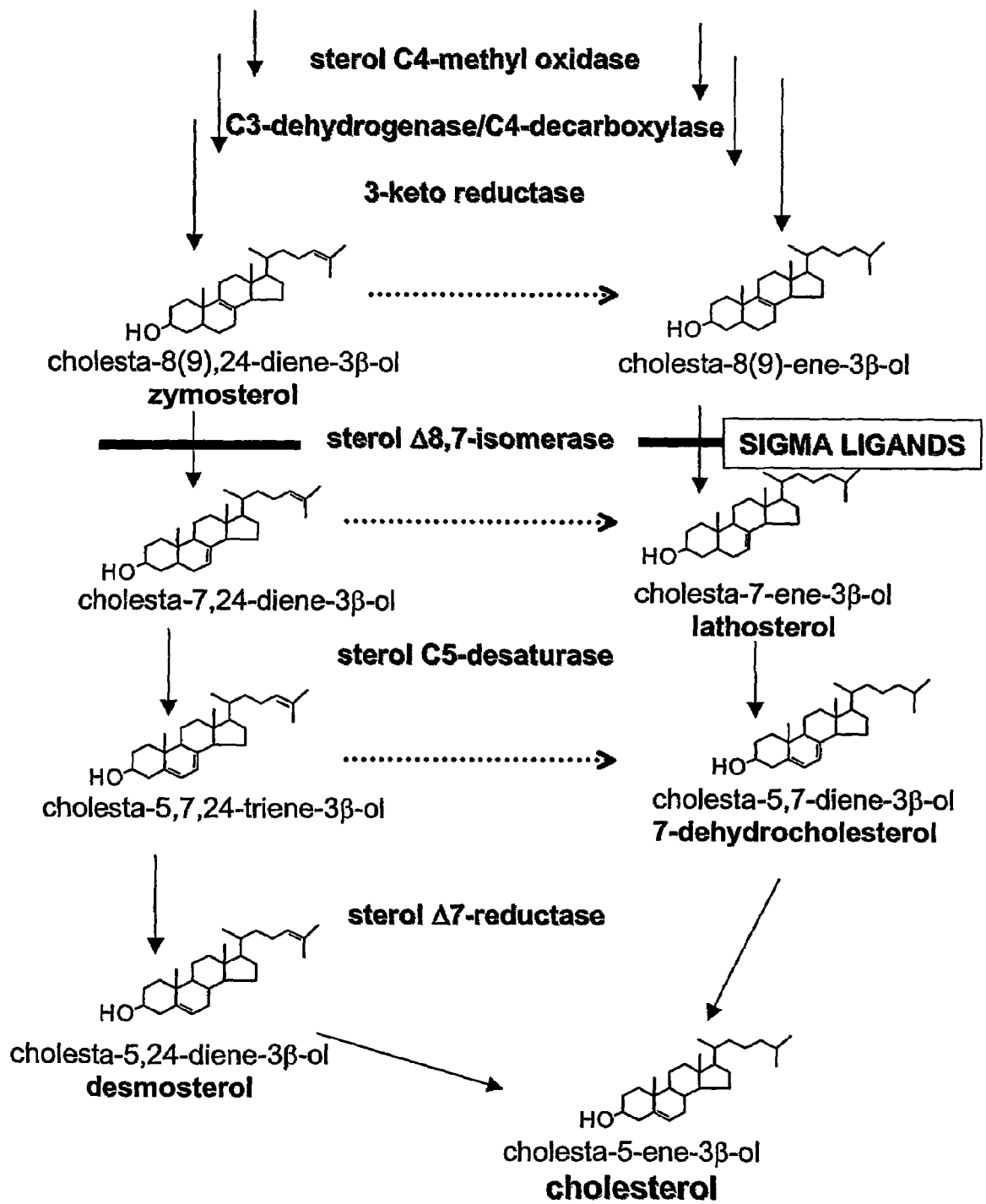

wherein n is an integer from 1 to 4;

$R_1$ is a hydrogen atom, hydroxyl group or lower $C_{1-6}$ alkoxy group;

$R_2$ is a hydrogen atom or a straight or branched lower $C_{1-6}$ alkyl group; and X is hydrogen, fluorine, chlorine, bromine, hydroxyl group, trifluoromethyl group, 3,4-di-Cl, 2,4-di-Cl or lower $C_{1-6}$ alkoxy group;

MATERIALS AND METHODS

Cell Culture and Addition of Sigma Ligands

The immortal human hepatocyte cell line $HepG_2$ was split to the 75 cm² flasks in the ratio 1:2, two flasks for each condition. The cells were cultured in the DMEM culture (L-arginine.HCl 0.084 g/l, L-cysteine.2HCl 0.0626 g/l, L-glutamine 0.584 g/l, glycine 0.03 g/l, L-histidine.HCl.$H_2O$ 0.042 g/l, L-isoleucine 0.105 g/l, L-leucine 0.105 g/l, L-lysine.HCl 0.146 g/l, L-methionine 0.03 g/l, L-phenylalanine 0.066 g/l, L-serine 0.042 g/l, L-threonine 0.095 g/l, L-thryptophan 0.016 g/l, L-tyrosine 2Na.2$H_2O$ 0.10379 g/l, L-valine 0.094 g/l, choline chloride 0.004 g/l, folic acid 0.004 g/l, myo-inositol 0.0072 g/l, niacinamide 0.004 g/l, D-pantothenic acid 0.004 g/l, pyridoxal.HCl 0.004 g/l, riboflavin 0.0004 g/l, thiamine.HCl 0.004 g/l, calcium chloride.2$H_2O$ 0.265 g/l, ferric nitrate.9$H_2O$ 0.0001 g/l, magnesium sulfate [anhydride] 0.09767 g/l, potassium chloride 0.4 g/l, sodium chloride 6.4 g/l, monobasic sodium phosphate [anhydride] 0.109 g/l, glucose 4.5 g/l and phenol red, Na 0.0159 g/l) with 5% bovine serum and 1% L-glutamine. After 24 hours a medium with 100 μM ligands of sigma receptors (BK-31.2HBr, BK-33.2HBr, BK-35.2HBr and BK-38.2HBr) was added to the cells. The known inhibitors of cholesterol biosynthesis, 100 μM lovastatin or pravastatin, both the inhibitors of HMG-CoA reductase, and 100 μM fluconazole that inhibits enzymes of the P450 family to which lanosterol 14α-demetylase (CYP51) also belongs, were used as positive controls. The cells grown in normal media without the addition of inhibitors served as negative control. The medium was exchanged after 24 hours. After 48 hours, 40 μCi [$^3$H] acetate was added per 1 ml of the medium (400 μCi per flask). The medium was aspirated after 24 hours, and the cells were tryptinized with 2 ml of trypsine. The cells were collected in 4 ml of the medium, centrifuged, and the cell pellet resuspended in distilled water (1 ml per flask). The cells were homogenized by freeze-thawing. Sterols were extracted from the homogenate. Protein concentration was determined in the homogenate with the Bio-rad reagent according to the recommended protocol of the producer.

Sterol Extraction

The homogenate was transferred into glass vials with an inert cover. 3 ml of the extraction solution (75% n-heptane: 25% isopropanol (vol/vol)) was added. The closed vials were shaken vigorously on a shaker in the dark room for 2 hours. After extraction the vials were centrifuged (2000 g, 10 min), the organic phase was transferred into the glass tubes, dried under nitrogen, washed with 2 ml of HPLC grade n-heptane, centrifuged (2000 g, 5 min) and transferred to a fresh glass tube. Until analysis, the samples were stored in the HPLC-grade solvent in dark and cold.

HPLC Analysis (HPLC stands for High Performance Liquid Chromatography)

The dried extracts were dissolved in 250 μl n-heptane. 100 μl aliquots were injected into the normal phase column (ChromSpher Si, 150 mm×3 mm, particle size 5 μm) with the mobile phase 99.5% n-heptane:0.5% isopropanol at flow rate 1 ml/min and room temperature.

Detection of Sterols

The sterols were detected by the UV detector at two wavelengths: 200 nm for lanosterol/T-MAS and cholesterol and 249 nm for 4,4-dimethyl-α-cholesta-8,14,24-triene-3β-ol (FF-MAS) and internal standard ergosterol. For determination of sterol after metabolic labeling, a radiodetector with the flow-through cell was used. Sterol determination was performed according to retention times of the standards: lanosterol (Steraloids), cholesterol (Steraloids), ergosterol (Sigma), 4,4-dimethyl-α-cholesta-8,14,24,-triene-3β-ol (FF-MAS) and [$^3$H] FF-MAS (laboratory source A. G. Byskov, Rikhospitalitet, University of Copenhagen). The results were normalized according to the quantity of internal standard ergosterol and the concentration of proteins in the homogenate. The results represent the average value of two measurements with appropriate standard deviation.

Results

Figure 3:
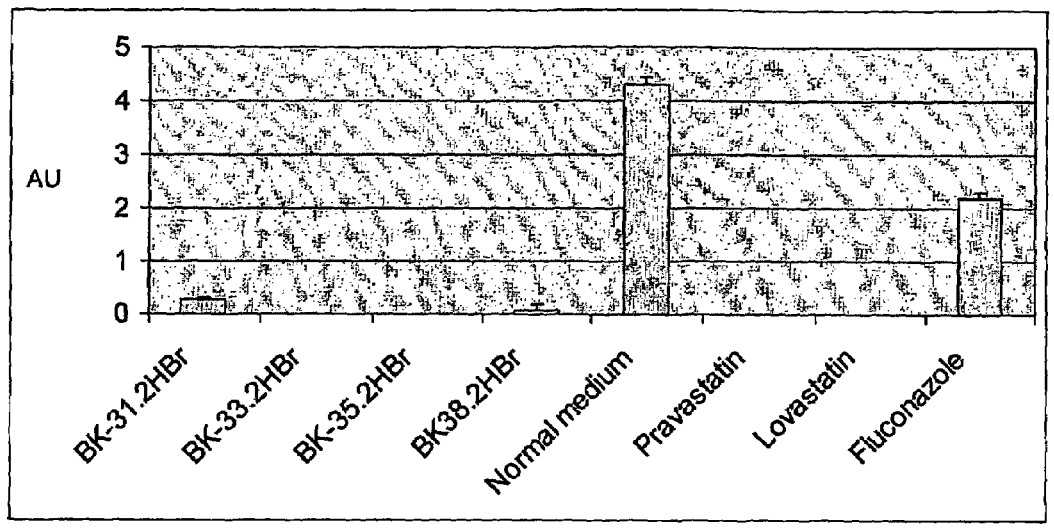
FIG. 3 is a graphical illustration with two graphs that depict amounts of radiolabeled cholesterol containing various inhibitors.
Figure 3:
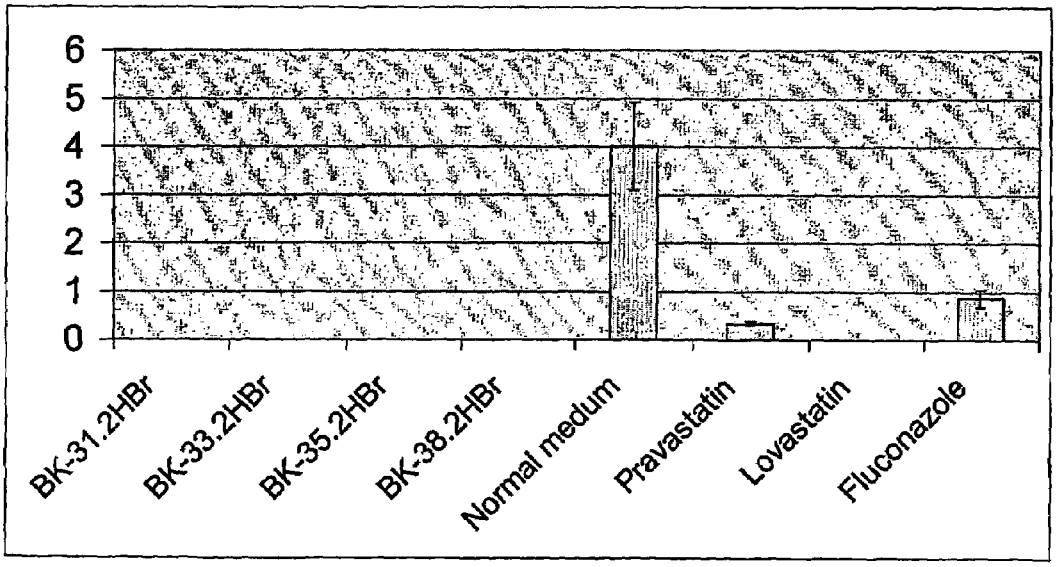
Figure 4:
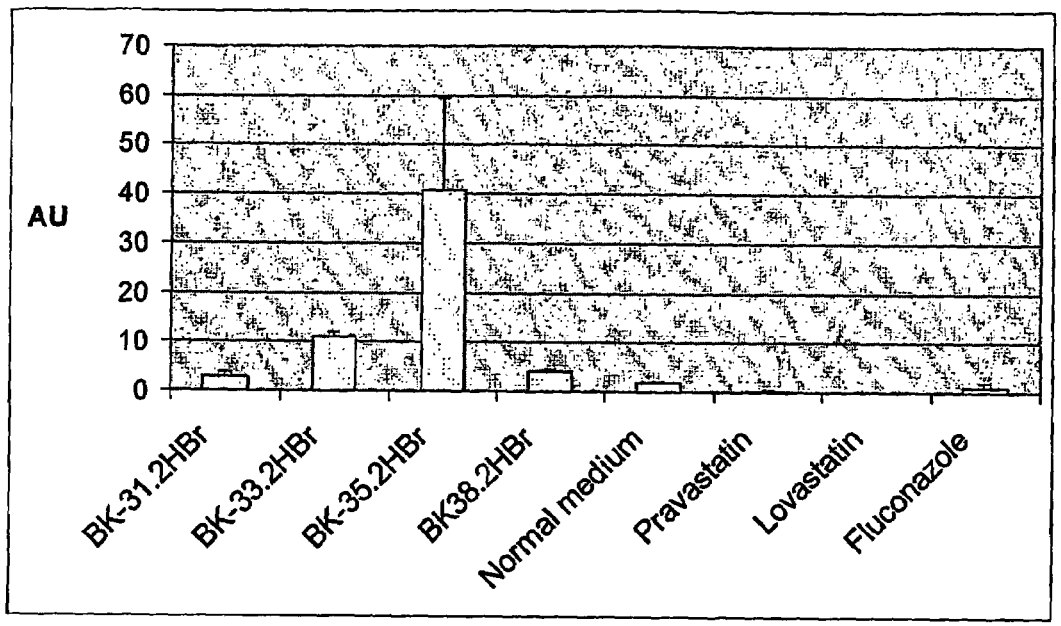
FIG. 4 is a graphical illustration with two graphs that depict amounts of radiolabeled intermediate sterol X eluted after cholesterol.
Figure 4:
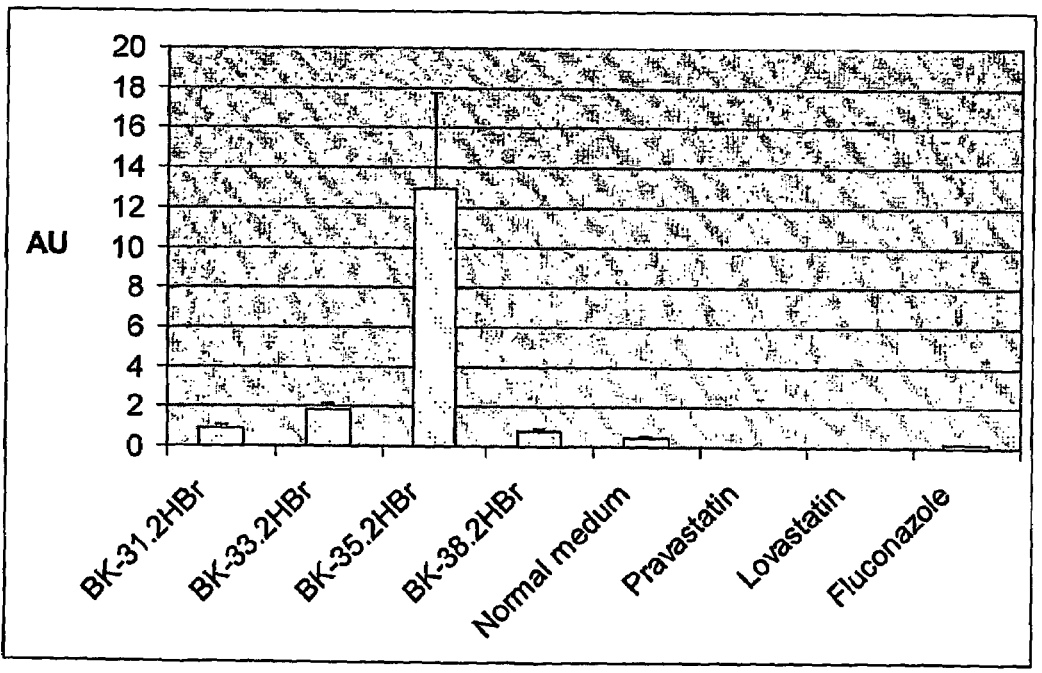
Figure 5:
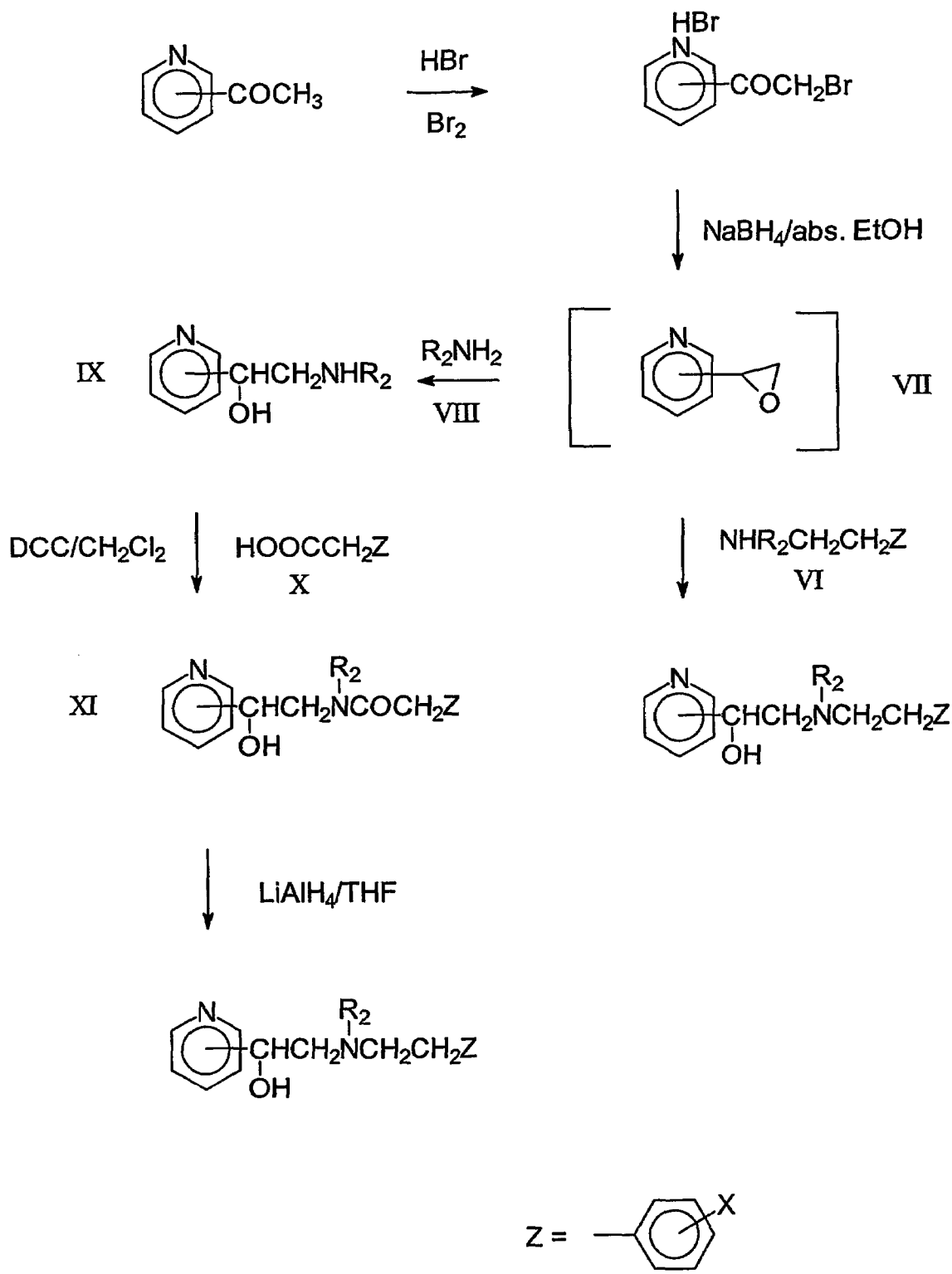
FIG. 5 is a schematic diagram showing aspects of a chemical process for making one or more derivatives of pyridylethanol (phenylethyl) amine of the formula
Figure 6:
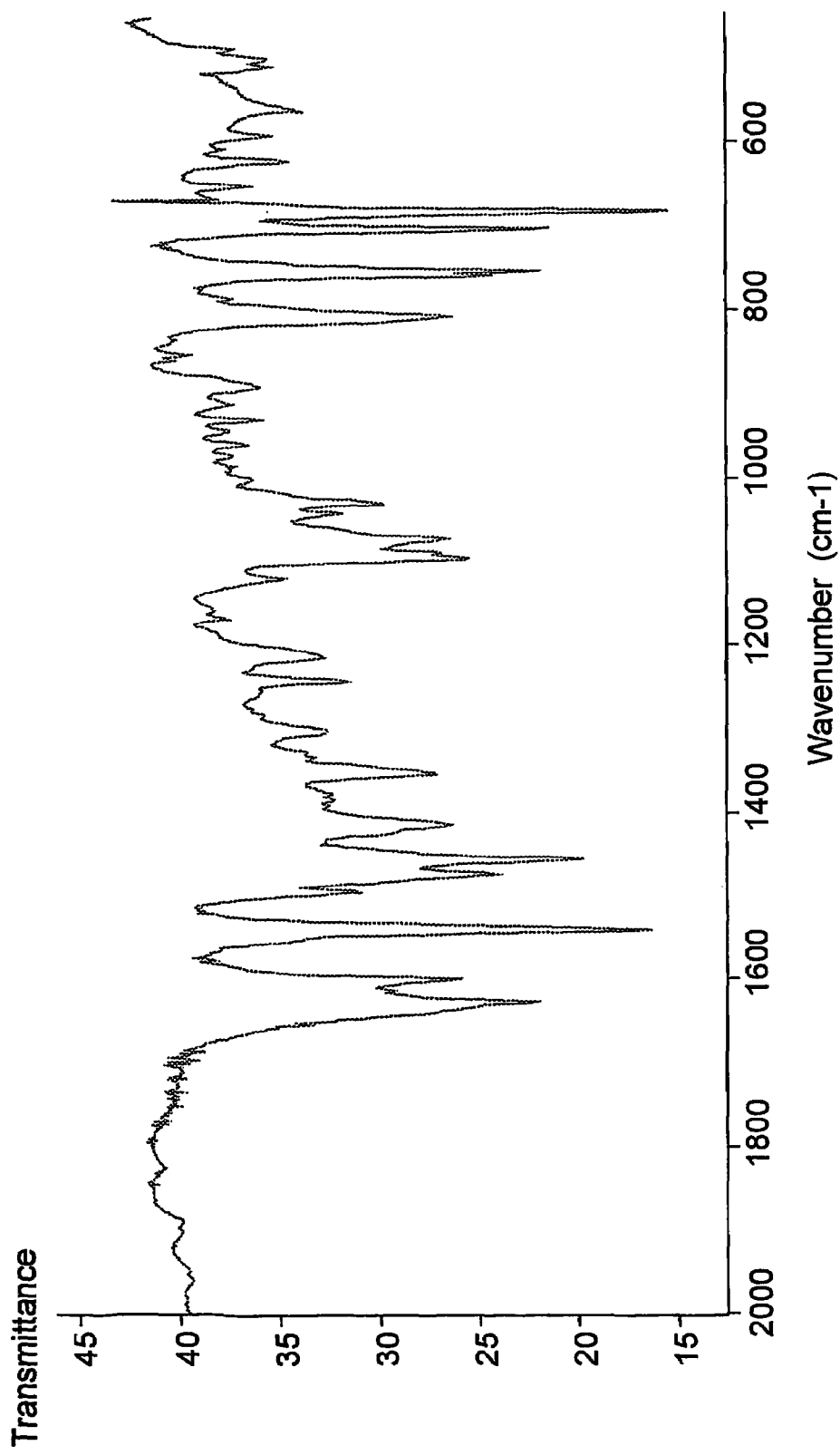
Figure 7:
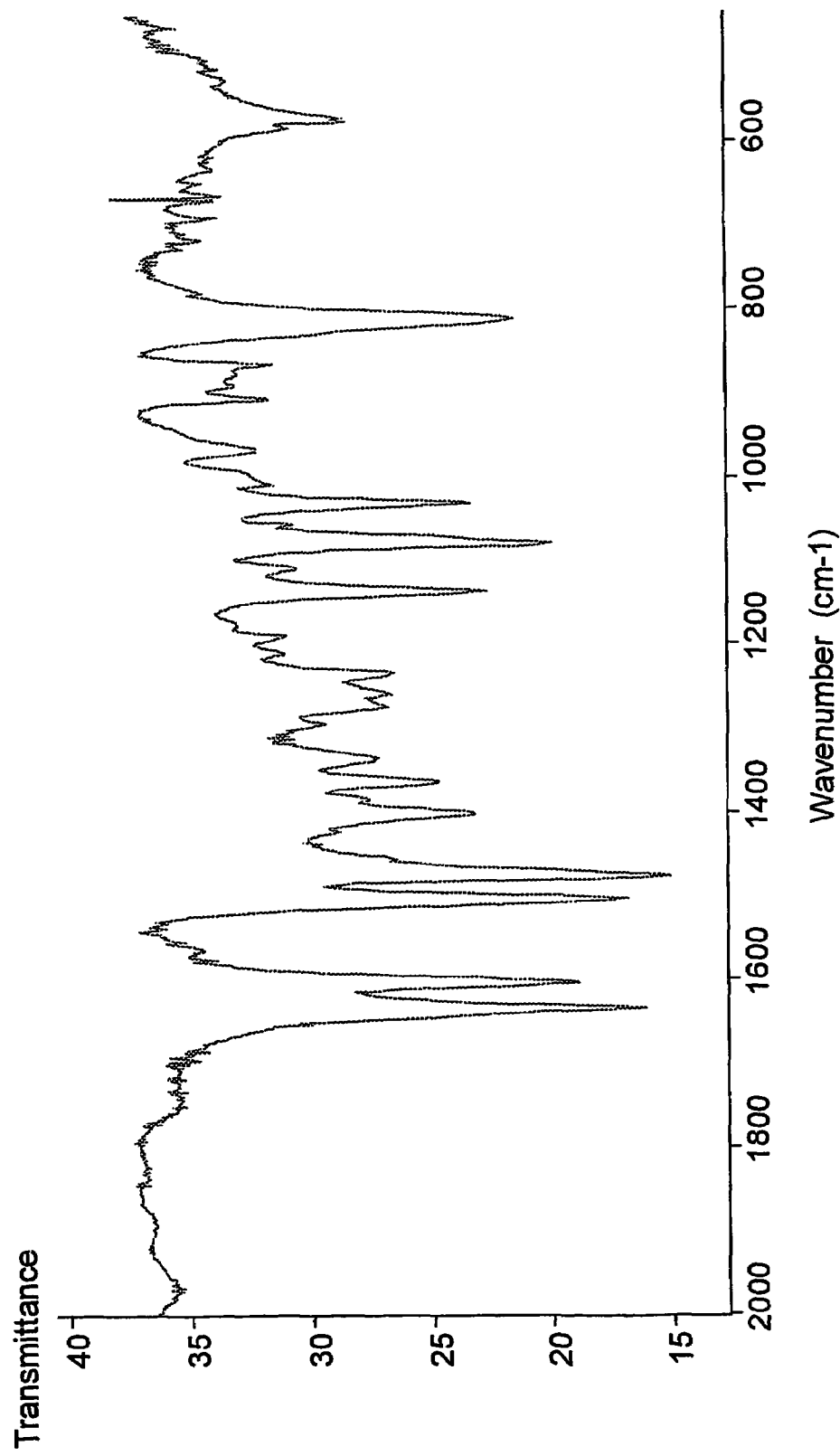
Figure 8:
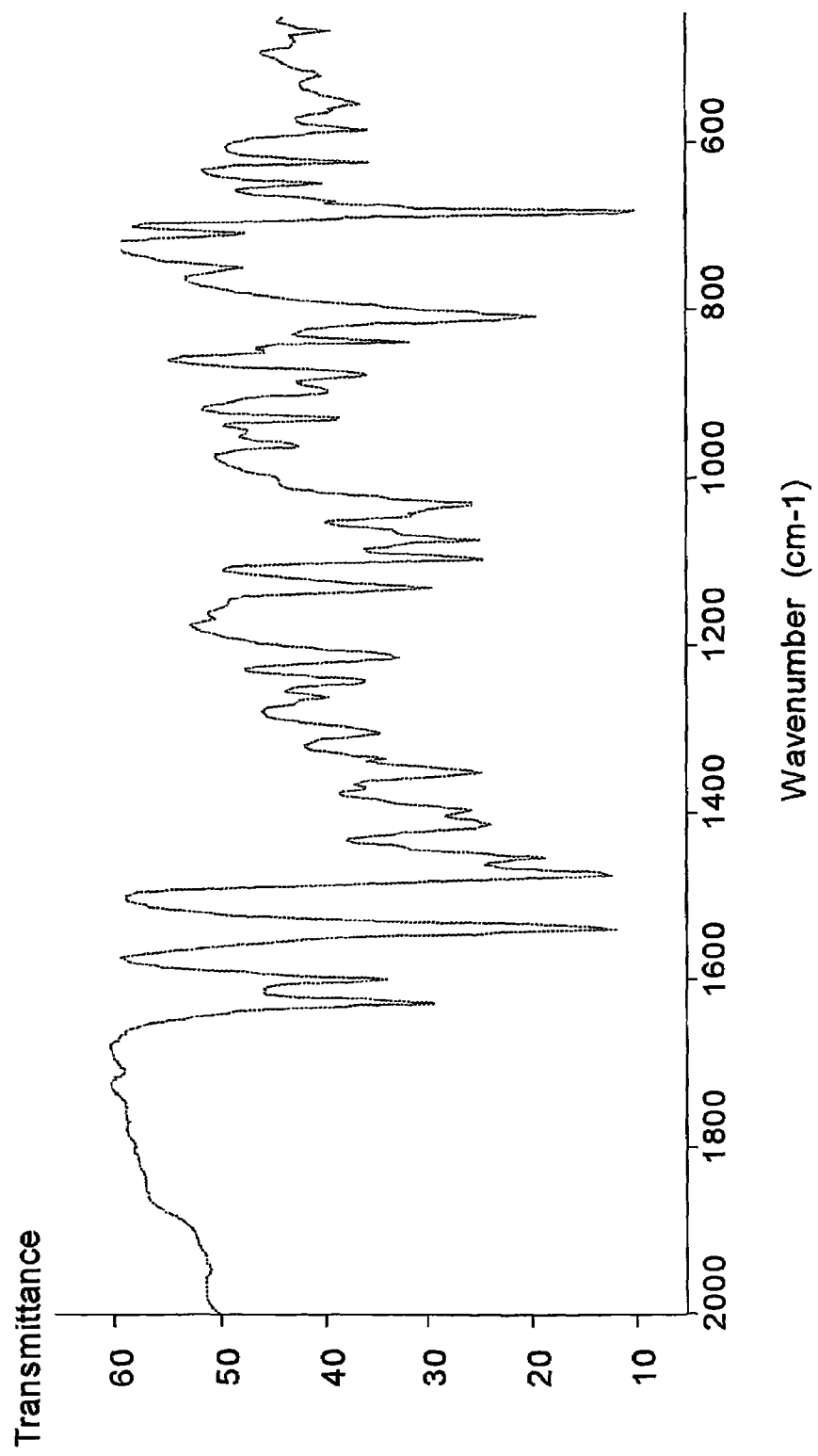
Figure 9:
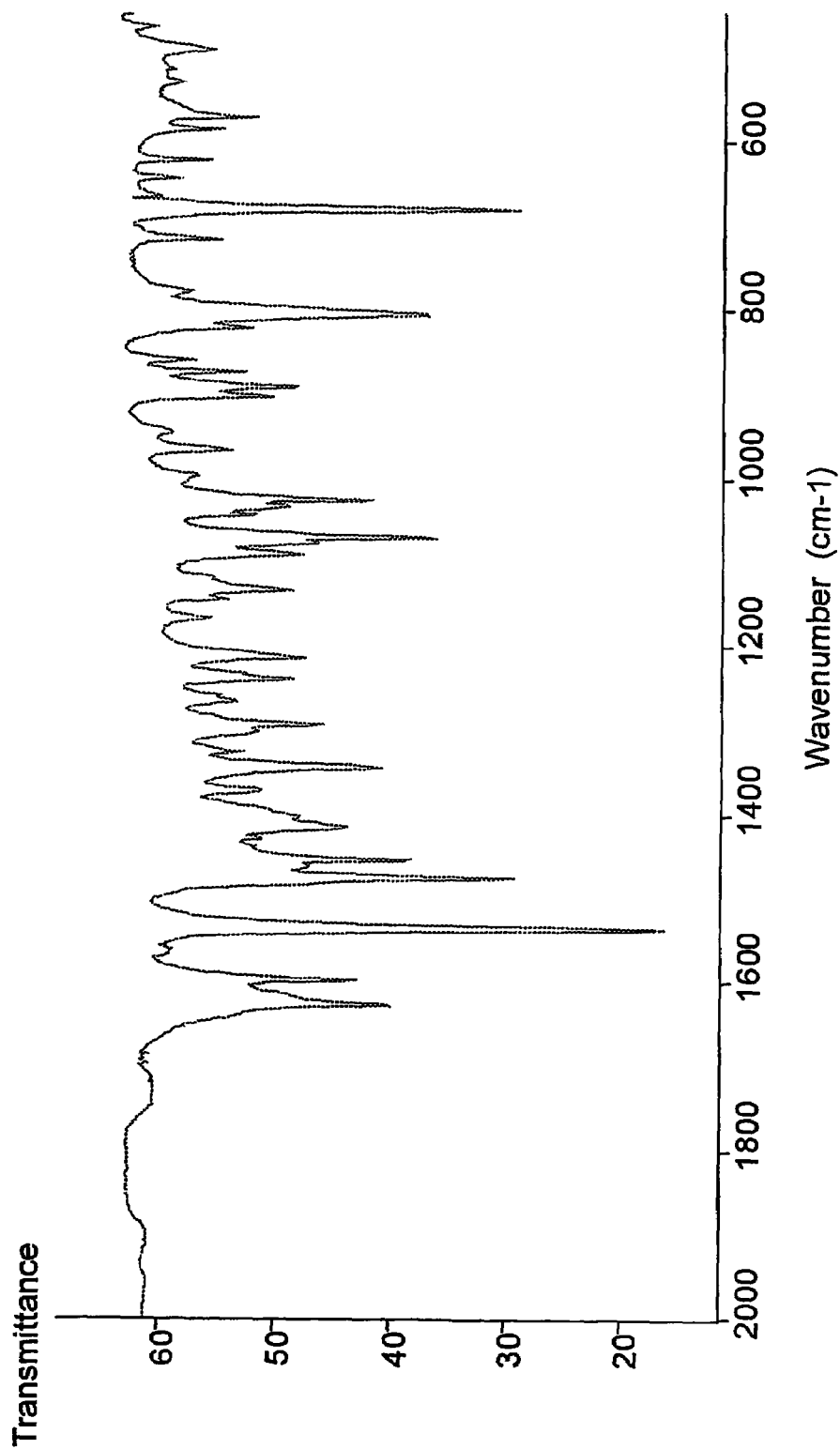

The metabolic labeling of the cells showed excellent results on the level of a lowered amount of synthesized cholesterol. Cholesterol had a peak on the radiodetector at about 6.0 min. FIG. 3 shows the quantity of radiolabelled cholesterol after metabolic labeling of the cells and the addition of different inhibitors. Negative control, normal medium—the medium without the addition of inhibitors, A—analysis 1, B—analysis 2. AU—arbitrary units. Cholesterol peak, as shown in FIG. 3, was significantly lowered in the cells with added sigma ligands, being the most pronounced by the compound with signature BK-35.2HBr. In addition to a complete block in cholesterol synthesis, as evident from FIG. 3, the tested compounds also showed an effect on accumulation of the early intermediates of the postsqualene portion of cholesterol biosynthesis. An increased amount of sterols representing lanosterol or 4,4-dimethyl-α-cholesta-8(9),24,-diene-3β-ol (T-MAS) was noted. The greatest influence was exhibited by the compound with signature BK-35.2HBr with the tenfold increase of the intermediate produced, as shown in FIG. 4. FIG. 4 shows the quantity of the radiolabelled intermediate sterol X that was eluted after cholesterol (7-dehydrocholesterol or lathosterol). The signatures are the same as in FIG. 3. A—analysis 1, B—analysis 2.

All analysis confirm that the novel derivatives of pyridylethanol (phenylethyl) amines as sigma ligands according to this invention block cholesterol synthesis most probably at the level of sterol Δ8,7-isomerase. In the presence of the compound with signature BK-35.2HBr the cholesterol quantity is diminished and the quantity of the intermediates residing before the sterol Δ8,7-isomerase step is increased.

The well known inhibitors of HMG-CoA-reductase (lovastatin and pravastatin) and lanosterol 14α-demethylase (fluconazole) served as positive controls for the accuracy of these analyses. Lovastatin and pravastatin completely blocked the biosynthesis, as shown in FIG. 3. Fluconazole, as expected, was a weaker inhibitor of cholesterol biosynthesis since it is not a specific inhibitor of the human lanosterol-14α demethylase. The quantity of lanosterol or 4,4-dimethyl-α-cholesta- 8(9),24,-diene-3β-ol (T-MAS) was not increased by the statins since these compounds block the biosynthesis at the level of HMG-CoA reductase which resides at the beginning of the cholesterol biosynthesis pathway, thus, before lanosterol and T-MAS.

CONCLUSIONS

We have determined that the cells grown in the presence of the tested compounds with the signatures BK-31.2HBr, BK-33.2HBr, BK-35.2HBr and BK-38.2HBr, synthesize significantly lowered amounts of cholesterol. On the basis of these results, we conclude that all tested compounds, that is, novel derivatives of pyridylethanol (phenylethyl) amines of this invention, are the inhibitors of cholesterol biosynthesis, most likely at the level of sterol Δ7,8-isomerase. The greatest lowering of cholesterol was observed by the compound with signature BK-35.2HBr, that is, 1-(3-pyridyl)-2-(N-(2-(3,4-dichlorophenyl)ethyl)-N-propylamino)ethanol dihydrobromide. The results attained in at least two independent experiments are reproducible and show that of all tested sigma ligands the compound with signature BK-35.2HBr is the best inhibitor of cholesterol biosynthesis of this invention and is thus particularly suitable for the treatment of hypercholesterolemia and hyperlipemia.

The invention claimed is:

1. A compound of formula I

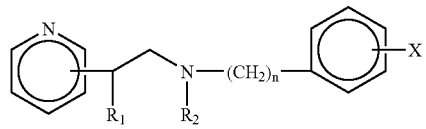

wherein n is an integer from 2 to 4

$R_1$ is a hydroxyl group or lower $C_{1-6}$ alkoxy group $R_2$ is a hydrogen atom or a straight or branched lower $C_{1-6}$ alkyl group X is hydrogen, fluorine, chlorine, bromine, hydroxyl group, trifluoromethyl group, 3,4-di-Cl,2,4-di-Cl or lower $C_{1-6}$ alkoxy group or an enantiomer, diastereoisomer or racemate thereof, or a physiologically acceptable acid addition salt thereof.

2. The compounds according to claim 1 in which n is an integer 2, $R_1$ is a hydroxyl group, $R_2$ a methyl, ethyl, n-propyl, isopropyl, n-butyl or isobutyl group and X is a hydrogen atom, 3,4-di-Cl, or 2,4-di-Cl.

3. The compound according to claim 1 in which $R_1$ is a hydroxyl group in the RS configuration.

4. The compound according to claim 1 which is 1-(3-pyridyl-2-(N-(2-(3,4-dichlorophenyl)ethyl-N-propylamino) ethanol and a dihydrobromide salt thereof.

5. The compound according to claim 1 which is 1-(3-pyridyl)-2-(N-(2-phenylethyl)-N-propylamino)ethanol and a dihydrobromide salt thereof.

6. The compound according to claim 1 which is 1-(3-pyridyl)-2-(N-(2-3,4-dichlorophenyl)ethyl-N-methylamino) ethanol and a dihydrobromide salt thereof.

7. The compound according to claim 1 which is 1-(4-pyridyl)-2-(N-(2-(3,4-dichlorophenyl)ethyl-N-methylamino)ethanol and a dihydrobromide salt thereof.

8. The compounds of formula I according to claim 1 and the physiologically acceptable acid addition salts thereof as the ligands of sigma receptors for inhibiting cholesterol biosynthesis in the treatment of hypercholesterolemia and hyperlipemia in humans.

9. The compositions comprising the compound of formula I according to claim 1 and the physiologically acceptable acid addition salts thereof.

10. The process for preparation of the compound of formula I according to claim 1 which process comprises a) alkylating secondary amines of formula VI

 VI wherein $R_2$ is as defined above in formula I and Z is a group

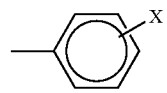

in which X is as defined above in formula I, with pyridyloxirane of formula VII

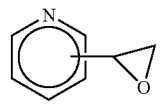 VII to form the compound of formula I, or b) alkylating primary amines of formula VIII

 VIII wherein $R_2$ is as defined above in formula I, with pyridyloxirane of formula VII

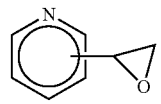 VII to intermediate compounds of formula IX

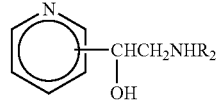 IX wherein $R_2$ is as defined above in formula I, and condensing with the derivatives of phenylacetic acid of formula X

 X wherein Z is as defined above,
to an intermediate compounds of formula XI
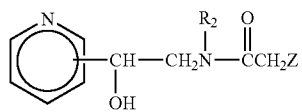
XI
and reducing the compound of formula XI to the compound of formula I and optionally converting the compound of formula I into or a physiologically acceptable acid addition salt thereof.
* * * * *

UNITED STATES PATENT AND TRADEMARK OFFICE
CERTIFICATE OF CORRECTION

PATENT NO. : 7,560,474 B2
APPLICATION NO. : 10/521294
DATED : July 14, 2009
INVENTOR(S) : Breda Rode et al.

It is certified that error appears in the above-identified patent and that said Letters Patent is hereby corrected as shown below:

In Claim 10 (at Column 16, line 66), delete "HOOCH2A" and insert therefor --HOOCH2Z--.

In Claim 3 (at Column 15, line 52), delete "compound" and insert therefor --compounds--.

In Claim 10 (at Column 17, line 2), delete "compounds" and insert therefor --compound--.

Signed and Sealed this

Twenty-second Day of December, 2009

David J. Kappos
*Director of the United States Patent and Trademark Office*